United States Patent
Jun et al.

(10) Patent No.: US 10,208,256 B2
(45) Date of Patent: Feb. 19, 2019

(54) METHOD FOR PREPARING MONOCYCLIC AROMATIC COMPOUNDS AND LONG-CHAIN OLEFIN COMPOUNDS FROM CARBON DIOXIDE-RICH SYNTHESIS GAS

(71) Applicant: KOREA RESEARCH INSTITUTE OF CHEMICAL TECHNOLOGY, Daejeon (KR)

(72) Inventors: Ki Won Jun, Daejeon (KR); Yun Jo Lee, Daejeon (KR); Geun Jae Kwak, Daejeon (KR); Hae Gu Park, Daejeon (KR); Yong Tae Kim, Anyang-si (KR); Seok Chang Kang, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 15/542,264

(22) PCT Filed: Nov. 27, 2015

(86) PCT No.: PCT/KR2015/012856
§ 371 (c)(1),
(2) Date: Jul. 7, 2017

(87) PCT Pub. No.: WO2016/111463
PCT Pub. Date: Jul. 14, 2016

(65) Prior Publication Data
US 2017/0355910 A1    Dec. 14, 2017

(30) Foreign Application Priority Data

Jan. 8, 2015 (KR) .................. 10-2015-0002900

(51) Int. Cl.
| | | |
|---|---|---|
| C10G 2/00 | (2006.01) | |
| C10G 69/04 | (2006.01) | |
| C07C 1/04 | (2006.01) | |
| C07C 1/12 | (2006.01) | |
| C10G 45/68 | (2006.01) | |
| C10G 11/05 | (2006.01) | |

(52) U.S. Cl.
CPC ............ *C10G 2/332* (2013.01); *C07C 1/0435* (2013.01); *C07C 1/12* (2013.01); *C10G 2/00* (2013.01); *C10G 2/50* (2013.01); *C10G 11/05* (2013.01); *C10G 45/68* (2013.01); *C10G 69/04* (2013.01); *C10G 2300/1022* (2013.01); *C10G 2400/22* (2013.01); *C10G 2400/30* (2013.01)

(58) Field of Classification Search
CPC ......... C07C 1/0435; C07C 1/12; C10G 11/05; C10G 2/00; C10G 2/332; C10G 2/50; C10G 45/68; C10G 69/04; C10G 2300/1022; C10G 2400/22; C10G 2400/30

See application file for complete search history.

(56) References Cited

U.S. PATENT DOCUMENTS

| | | | |
|---|---|---|---|
| 8,609,738 B2 * | 12/2013 | Mamedov | C01B 3/382 518/700 |
| 2003/0181325 A1 | 9/2003 | Ou et al. | |
| 2013/0324772 A1 | 12/2013 | Huber et al. | |

FOREIGN PATENT DOCUMENTS

| | | |
|---|---|---|
| JP | 3-2128 A | 1/1991 |
| JP | 3-26791 A | 2/1991 |
| JP | 3-52993 A | 3/1991 |
| JP | 5-43484 A | 2/1993 |
| JP | H06346062 A * | 12/1994 |
| JP | 2007-190520 A | 8/2007 |
| JP | 2012-62255 A | 3/2012 |
| JP | 2012-201802 A | 10/2012 |
| KR | 10-2014-0027082 A | 3/2014 |
| KR | 10-1418911 B1 | 7/2014 |
| WO | 00/18853 A1 | 4/2000 |
| WO | 2005/094992 A1 | 10/2005 |

OTHER PUBLICATIONS

JPH06346062A, Dec. 12, 1994, pp. 1-13; English translation (Year: 1994).*
D.H. Chun et al.; "Highly selective iron-based Fischer-Tropsch catalysts activated by CO2-containing syngas"; Journal of Catalysis 317 (2014); pp. 135-143.
International Search Report dated Mar. 28, 2016, corresponding to International Publication No. PCT/KR2015/012856, citing the above reference(s).
Written Opinion of the International Searching Authority dated Mar. 28, 2016, corresponding to International Publication No. PCT/KR2015/012856, citing the above reference(s).

(Continued)

*Primary Examiner* — Medhanit W Bahta
(74) *Attorney, Agent, or Firm* — Hauptman Ham, LLP

(57) ABSTRACT

Disclosed is a method for directly synthesizing monocyclic aromatic compounds and long-chain olefin compounds from a carbon dioxide-rich synthetic gas and, specifically, a method for directly synthesizing monocyclic aromatic compounds and long-chain olefin compounds from a carbon dioxide-rich synthetic gas, the method comprising a step of preparing a $C_1$-$C_{15}$ short-chain hydrocarbon by Fischer-Tropsch (FT) synthesis and a step of preparing monocyclic aromatic compounds and long-chain olefin compounds by dehydrogenating the short-chain hydrocarbon products, and maximizing the yield of the short-chain hydrocarbon by using, as a synthetic gas to be used in FT synthesis, a carbon dioxide-rich synthetic gas in which the molar ratio of hydrogen, carbon monoxide and carbon dioxide is delimited to a specific range, and maximizing the yield of the monocyclic aromatic compounds or the long-chain olefin compounds by specifying the composition of a catalyst to be used in the dehydrogenation and the temperature and pressure condition.

12 Claims, 1 Drawing Sheet

(56) References Cited

OTHER PUBLICATIONS

Chun, et al., "Negative effects of CO2 in the feed stream on the Catalytic Performance of Precipitated Iron-Based catalysts for Fischer-Tropsch synthesis"; Catal. Lett (2012) 142: pp. 452-459.

Gnanamani, et al., "Fischer Tropsch synthesis: Effect of CO2 containing syngas over Pt promoted Co/y-Al2O3 and K-promoted Fe catalysts"; Catalysis communications 12 (2011), pp. 936-939.

Liu, et al., "Effect of co-feeding carbon dioxide on Fischer-Tropsch synthesis over an ironmanganese catalyst in a spinning basket reactor"; Fuel processing technology 89 (2008), pp. 234-241.

Extended European Search Report dated Jul. 3, 2018, corresponding to European Application No. 15877183.2 citing the above reference(s).

* cited by examiner

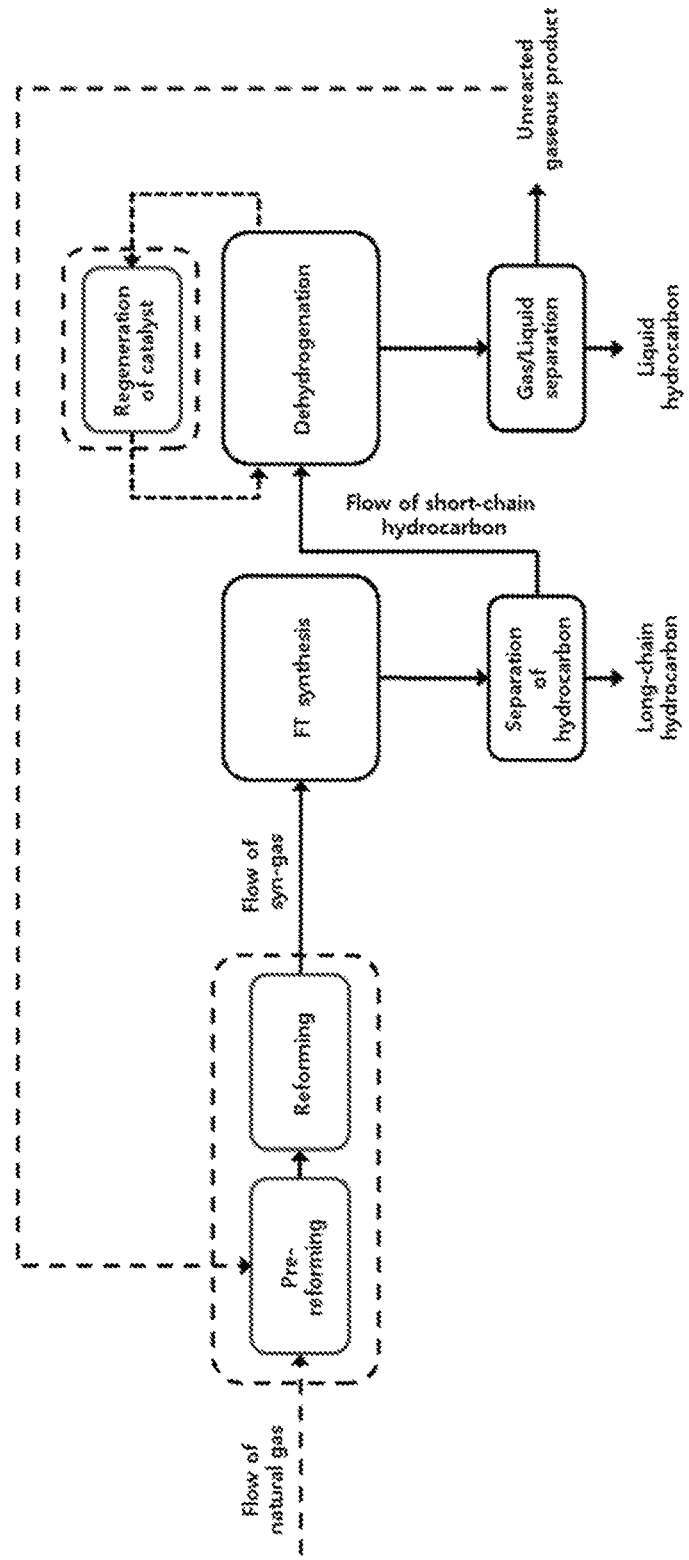

METHOD FOR PREPARING MONOCYCLIC AROMATIC COMPOUNDS AND LONG-CHAIN OLEFIN COMPOUNDS FROM CARBON DIOXIDE-RICH SYNTHESIS GAS

CROSS REFERENCE TO RELATED APPLICATION

This present application is a national stage filing under 35 U.S.C. § 371 of PCT application number PCT/KR2015/012856 filed on Nov. 27, 2015 which is based upon and claims the benefit of priority to Korean Patent Application No. 10-2015-0002900 filed on Jan. 8, 2015 in the Korean Intellectual Property Office. The disclosures of the above-listed applications are hereby incorporated by reference herein in their entirety.

TECHNICAL FIELD

The present invention relates to a method for directly synthesizing monocyclic aromatic compounds and long-chain olefin compounds from a carbon dioxide-rich synthesis gas, more particularly to a process of preparing a hydrocarbon through a Fischer-Tropsch (FT) synthesis process and a process of preparing monocyclic aromatic compounds and long-chain olefin compounds through a hydrocarbon dehydrogenation process, wherein a carbon dioxide-rich synthesis gas with the molar ratio of hydrogen, carbon monoxide and carbon dioxide limited to a particular range is used as a synthesis gas used for the Fischer-Tropsch (FT) synthesis process to maximize the yield of $C_1$-$C_{15}$ short-chain hydrocarbons and the composition of a catalyst used in the dehydrogenation process as well as the temperature and pressure conditions thereof are specified to maximize the yield of monocyclic aromatic compounds or long-chain olefin compounds.

BACKGROUND ART

Because carbon dioxide ($CO_2$) is the most significant greenhouse gas, technologies for sequestration and reducing carbon dioxide through capture, storage, conversion, etc. are actively being proposed. Among them, the GTL (gas to liquids) process is drawing attentions as an important technology for providing hydrocarbons obtained from petroleum resources with the recent development of shale gas.

The Fischer-Tropsch (FT) synthesis process, a critical process in the GTL technology, is a process whereby hydrocarbons are produced from a synthesis gas produced through reforming of natural gas. However, additional separation and upgrading processes are necessary because the hydrocarbons produced through the FT synthesis process are various in the number of carbon atoms. Therefore, for simplification of the GTL process and effective hydrocarbon production, studies are actively being conducted on the synthesis of hydrocarbons with a relatively narrow carbon number range by optimizing the condition of the FT synthesis process.

In the FT synthesis process, iron-based catalysts and cobalt-based catalysts are mainly used. Although iron-based catalysts were used mainly in the early stage of development, cobalt-based catalysts are mainly used recently. However, because the synthesis gas which is used as a source material in the FT synthesis process using cobalt-based catalysts should have a $H_2$/CO molar ratio close to 2, it is difficult to satisfy the operating condition. In addition, because the use of carbon dioxide contained in the synthesis gas is not considered, both thermal and carbon efficiency for the overall process are relatively low and secondary environmental problems may occur. In contrast, the FT synthesis process using iron-based catalysts is an environment-friendly process with relatively high thermal efficiency and carbon efficiency because carbon dioxide can be converted to hydrocarbons by water gas shift reaction [see patent document 1].

Monocyclic aromatic compounds such as benzene, toluene, xylene, ethylbenzene, etc. or olefin compounds are used as source materials for petrochemicals such as synthetic fibers, plastics, gasoline additives, etc. In the existing methods, monocyclic aromatic compounds or olefin compounds are produced mainly from mixed fuel oil.

As the methods for preparing monocyclic aromatic compounds, patent documents 2-5 propose preparation from polycyclic aromatic compounds contained in light cycle oil (LCO), etc. using zeolite catalysts. However, the methods proposed in the patent documents 2-5 have the problems that the yield of monocyclic aromatic compounds is not high and the catalyst is easily deactivated during the reaction due to carbon deposition.

As the methods for preparing olefin compounds, patent documents 6-8 propose preparation of light olefins such as ethylene, propylene, etc. from naphtha or heavy hydrocarbons using zeolite catalysts. However, the preparation of long-chain olefin compounds with 6-17 carbon atoms is not described at all in the patent documents 6-8.

REFERENCES OF THE RELATED ART

Patent Documents (Patent document 1) Korean Patent Registration No. 10-01418911. "Hydrocarbon compounds prepared by Fischer-Tropsch synthesis and method for preparing the same".
(Patent document 2) Japanese Patent Publication No. 1991-002128. "Method for preparing aromatic-containing short-chain hydrocarbons".
(Patent document 3) Japanese Patent Publication No. 1991-052993. "Method for preparing hydrocarbons rich in BTX".
(Patent document 4) Japanese Patent Publication No. 1991-26791. "Method for preparing hydrocarbons".
(Patent document 5) Korean Patent Publication No. 10-2014-0027082. "Catalyst for preparing monocyclic aromatic hydrocarbons and method for preparing monocyclic aromatic hydrocarbons".
(Patent document 6) International Patent Publication No. WO2000-18853. "Process for manufacturing olefins using pentasil zeolite-based catalyst".
(Patent document 7) International Patent Publication No. WO2005-94992. "Catalyst containing zeolite for hydrocarbon converting, preparation thereof and hydrocarbon oil converting method using the catalyst".
(Patent document 8) Japanese Patent Publication No. 2007-190520. "Catalyst for catalytic cracking of heavy oil and method for preparing olefin and fuel oil".

DISCLOSURE

Technical Problem

The present invention is directed to providing a method for directly synthesizing monocyclic aromatic compounds and long-chain olefin compounds using a synthesis gas as a source material.

Technical Solution

In an aspect, the present invention provides a method for synthesizing monocyclic aromatic compounds and long-chain olefin compounds from a carbon dioxide-rich synthesis gas, which includes:

i) a step of preparing a hydrocarbon by conducting a Fischer-Tropsch (FT) synthesis process in the presence of an iron-based catalyst using a carbon dioxide-rich synthesis gas with a $CO_2/(CO+CO_2)$ molar ratio controlled within a range from 0.4 to 0.65 as a source material;

ii) a step of separating a $C_1$-$C_{15}$ short-chain hydrocarbon from the hydrocarbon products; and iii) a step of preparing $C_6$-$C_{12}$ monocyclic aromatic compounds and $C_6$-$C_{18}$ long-chain olefin compounds by dehydrogenating the $C_1$-$C_{15}$ short-chain hydrocarbon in the presence of a crystalline aluminosilicate-based catalyst, hydrogen and water.

Advantageous Effects

The present invention provides an effect of synthesizing highly value-added monocyclic aromatic compounds and long-chain olefin compounds with high yield by using a synthesis gas as a source material.

The present invention also provides an effect of maximizing carbon efficiency because the carbon dioxide contained in the synthesis gas with high content is converted to carbon monoxide by reverse water gas shift reaction in an FT synthesis process.

The FIGURE schematically describes a method for synthesizing a monocyclic aromatic compound and a long-chain olefin compound from a carbon dioxide-rich synthesis gas according to the present invention.

Accordingly, the preparation method of the present invention can reduce the carbon dioxide greenhouse gas and, at the same time, provide highly value-added monocyclic aromatic compounds and long-chain olefin compounds.

BRIEF DESCRIPTION OF DRAWINGS

FIG. 1 schematically describes a method for synthesizing monocyclic aromatic compounds and long-chain olefin compounds from a carbon dioxide-rich synthesis gas according to the present invention.

BEST MODE FOR CARRYING OUT INVENTION

Hereinafter, a synthesis method according to the present invention is described in detail referring to the FIGURE.

In the first step, a hydrocarbon is produced by conducting a Fischer-Tropsch (FT) synthesis process using a synthesis gas as a source material.

A general FT synthesis process is conducted by hydrogenation of carbon monoxide. However, in the present invention, carbon efficiency is maximized by an FT synthesis process in which carbon monoxide and carbon dioxide are hydrogenated at the same time.

Hydrogenation of carbon monoxide: $nCO + 2nH_2 \rightarrow (CH_2)_n + nH_2O$ (1)

Reverse water gas shift reaction: $CO_2 + H_2 \rightarrow CO + H_2O$ (2)

In the FT synthesis process of the present invention, a synthesis gas with a controlled molar ratio of hydrogen, carbon monoxide and carbon dioxide is used as a source material in the presence of an iron-based catalyst.

The iron-based catalyst is a catalyst commonly used in the FT synthesis process. The iron-based catalyst may further contain one or more promoter selected from a group consisting of copper (Cu), manganese (Mn), cobalt (Co), nickel (Ni), zinc (Zn), aluminum (Al) and potassium (K), if necessary.

The synthesis gas used as the source material in the present invention is a carbon dioxide-rich synthesis gas which contains hydrogen, carbon monoxide and carbon dioxide and has a $CO_2/(CO+CO_2)$ molar ratio of 0.4-0.65 and a $H_2/(2CO+3CO_2)$ molar ratio of 0.85-1.1. The synthesis gas may be produced through a reforming process of natural gas. Methods for reforming the natural gas may include steam reforming, carbon dioxide reforming, combined reforming, partial oxidation, etc. In particular, a synthesis gas produced by the combined reforming method which allows control of the composition of the synthesis gas may be used.

In the synthesis gas used in the present invention, if the $CO_2/(CO+CO_2)$ molar ratio is smaller than 0.4, the maximum carbon efficiency desired by the present invention cannot be achieved because the reverse water gas shift reaction whereby carbon dioxide is converted to carbon monoxide does not occur sufficiently. In addition, the catalyst lifetime may decrease due to increased carbon deposition. On the contrary, if the $CO_2/(CO+CO_2)$ molar ratio exceeds 0.65, productivity may decrease because both CO and $CO_2$ conversion decreased.

And, if the $H_2/(2CO+3CO_2)$ molar ratio in the synthesis gas is smaller than 0.85, the maximum carbon efficiency desired by the present invention cannot be achieved because the reverse water gas shift reaction whereby carbon dioxide is converted to carbon monoxide does not occur sufficiently. In addition, the catalyst life time may decrease due to increased carbon deposition. On the contrary, if the $H_2/(2CO+3CO_2)$ molar ratio exceeds 1.1, the yield of the long-chain olefin compounds may decrease because the selectivity of methane ($C_1$) is increased unnecessarily and, as a result, the selectivity of the short-chain olefin is increased during the following dehydrogenation of the hydrocarbon.

The FT synthesis process of the present invention is performed under the condition of a reaction temperature of 250-350° C. and a reaction pressure of 10-30 bar, specifically under the condition of a reaction temperature of 300-350° C. and a reaction pressure of 15-25 bar.

If the reaction temperature in the FT synthesis process is below 250° C., the maximum carbon efficiency desired by the present invention cannot be achieved because the reverse water gas shift reaction whereby carbon dioxide is converted to carbon monoxide does not occur sufficiently. In addition, the yield of the long-chain olefin compounds may decrease because the selectivity of methane ($C_1$) is increased unnecessarily. On the contrary, if the reaction temperature exceeds 350° C., the catalyst life time may decrease due to increased carbon deposition and the yield of the long-chain olefin compounds may decrease because the selectivity of methane ($C_1$) is increased.

If the reaction pressure in the FT synthesis process is below 10 bar, the maximum carbon efficiency desired by the present invention cannot be achieved because the reverse water gas shift reaction does not occur sufficiently. In addition, the yield of the long-chain olefin compounds may decrease because the selectivity of methane ($C_1$) is increased and the catalyst life time may decrease due to increased carbon deposition. On the contrary, if the reaction pressure exceeds 30 bar, the productivity of the monocyclic aromatic compounds and the long-chain olefin compounds decreases due to decreased selectivity of the short-chain hydrocarbon which is a reactant in the following dehydrogenation of the hydrocarbon. In addition, the operation of the process for maintaining the high pressure is complicated.

In the second step, a $C_1$-$C_{15}$ short-chain hydrocarbon is separated from the hydrocarbon produced in the FT synthesis process.

Because the reaction condition of the FT synthesis process of the present invention is controlled to improve the selectivity of the short-chain hydrocarbon, the selectivity of the $C_1$-$C_{15}$ short-chain hydrocarbon can be increased to 80-100%. Accordingly, the preparation method of the present invention achieves the effect of simplifying the process because an additional process for upgrading the hydrocarbon produced from the FT synthesis process is not necessary.

In the second step of the present invention, the $C_1$-$C_{15}$ short-chain hydrocarbon is separated and purified through simple separation in order to further increase the selectivity of the monocyclic aromatic compounds and the long-chain olefin compounds produced in the following dehydrogenation process.

The separation of the short-chain hydrocarbon is achieved through a separation process. Assuming that the pressure inside a reactor is 20 bar, the separation temperature may be maintained at 0-200° C., specifically 120-160° C.

If the separation temperature is below 0° C., the selectivity of the monocyclic aromatic compounds and the long-chain olefin compounds may decrease and the separator may be damaged due to freezing of water which is a reaction byproduct. On the contrary, if the separation temperature exceeds 200° C., the catalyst life time may decrease due to deposition of the long-chain hydrocarbon on the catalyst in the following dehydrogenation process.

In the third step, the monocyclic aromatic compounds and the long-chain olefin compounds are produced by dehydrogenating the short-chain hydrocarbon.

The dehydrogenation reaction consists of a step of reacting the short-chain hydrocarbon with hydrogen ($H_2$) and water ($H_2O$) in the presence of a crystalline aluminosilicate-based catalyst.

Based on the short-chain hydrocarbon used as the reactant, the hydrogen ($H_2$) is used with a molar ratio of 0.1-10, specifically 1-8, and the water ($H_2O$) is used with a molar ratio of 0.1-1.3, specifically 0.1-0.8.

If the hydrogen/short-chain hydrocarbon molar ratio during the dehydrogenation reaction is below 0.1 or exceeds 10, the selectivity of the monocyclic aromatic compounds and the long-chain olefin compounds may decrease because the dehydrogenation reaction does not occur sufficiently.

If the water/short-chain hydrocarbon molar ratio is below 0.1, the aluminosilicate-based catalyst may be deactivated quickly because it is difficult to remove carbon deposition with the water. And, if the water/short-chain hydrocarbon molar ratio exceeds 1.3, the catalyst may be deactivated quickly because an excess amount of water is adsorbed to the aluminosilicate-based catalyst.

As the catalyst used in the dehydrogenation reaction, a crystalline aluminosilicate-based catalyst with a Si/Al molar ratio of 10-50 is used. If the Si/Al molar ratio is below 10, the productivity of the polycyclic aromatic compounds is high because the dehydrogenation reaction proceeds vigorously. On the contrary, if the Si/Al molar ratio exceeds 50, the productivity of the monocyclic aromatic compounds decreases because the chain growth reaction becomes dominant.

Also, as the crystalline aluminosilicate-based catalyst, one with a Brønsted acid site/Lewis acid site ratio controlled to 0.1-3.2 is used. If the acid site ratio is below 0.1, the productivity of the polycyclic aromatic compounds is high because the dehydrogenation reaction proceeds vigorously. On the contrary, if the acid site ratio exceeds 3.2, the productivity of the monocyclic aromatic compounds decreases because the chain growth reaction becomes dominant.

Also, as the crystalline aluminosilicate-based catalyst, a crystalline porous catalyst containing mesopores with a size of 10 nm or smaller and micropores with a size of 1-8 Å. If the pore size of the crystalline catalyst does not satisfy the above range, the productivity of the monocyclic aromatic compounds decreases.

Although the crystalline aluminosilicate-based catalyst may be used alone, the crystalline aluminosilicate-based catalyst may further contain one or more promoter selected from a group consisting of iron (Fe), copper (Cu), zinc (Zn), tin (Sn), nickel (Ni), molybdenum (Mo), potassium (K), lanthanum (La), platinum (Pt), gold (Au), palladium (Pd), rhodium (Rd), ruthenium (Ru) and silver (Ag), if necessary. Specifically, the content of the metal element (A) contained as the promoter may be maintained such that the A/Al molar ratio based on the aluminum (Al) atom of the crystalline aluminosilicate-based catalyst is 0.01-2.5. Specifically, the molar ratio of the promoter metal element (A) based on the aluminum atom (i.e., A/Al molar ratio) may be 0.1-1.

The dehydrogenation process of the present invention is performed under the condition of a reaction temperature of 100-450° C. and a reaction pressure of 1-30 bar. By changing the reaction temperature and the reaction pressure of the dehydrogenation process, the selectivity of the monocyclic aromatic compounds or the long-chain olefin compounds can be controlled.

That is to say, in order to increase the selectivity of the monocyclic aromatic compounds, it is recommended to maintain the reaction temperature high and maintain the reaction pressure low within the above-described ranges of the reaction temperature and the reaction pressure. Specifically, the selectivity of the monocyclic aromatic compounds may be maximized by maintaining the reaction temperature at 300-350° C. and the reaction pressure at 5-20 bar.

And, in order to increase the selectivity of the long-chain olefin compounds, it is recommended to maintain the reaction temperature low and maintain the reaction pressure high within the above-described ranges of the reaction temperature and the reaction pressure. Specifically, the selectivity of the $C_6$-$C_{18}$ long-chain olefin compounds may be maximized by maintaining the reaction temperature at 200-270° C. and the reaction pressure at 10-20 bar or by maintaining the reaction temperature at 300-350° C. and the reaction pressure at 1-2 bar.

Accordingly, in the dehydrogenation process of the present invention, the yield of the monocyclic aromatic compounds or the $C_6$-$C_{18}$ long-chain olefin compounds may be maximized by optimizing the composition of the catalyst, the reaction temperature and the reaction pressure.

Among the hydrocarbons produced from the dehydrogenation process, light hydrocarbons ($C_1$-$C_4$) are included as byproducts in addition to the monocyclic aromatic compounds and the long-chain olefin compounds. In the present invention, the light hydrocarbons ($C_1$-$C_4$) in gas state and the monocyclic aromatic compounds and the long-chain olefin compounds in liquid state can be separated through a simple separation process.

Specifically, the separation temperature for the gas/liquid separation may be −5 to 5° C. If the temperature is below −5° C., the separator may be damaged due to freezing of water which is a reaction byproduct. And, if the temperature exceeds 5° C., the light hydrocarbon ($C_1$-$C_4$) may not be easily separated from the liquid hydrocarbon ($C_{5+}$).

The $C_1$-$C_4$ light hydrocarbon separated through the gas/liquid separation may be recycled to a reforming reactor for preparing the synthesis gas.

The synthesis method of the present invention described above will be described in more detail referring to the following examples. However, the present invention is not limited by them.

BEST MODE FOR CARRYING OUT INVENTION

Examples

Example 1. Fischer-Tropsch Synthesis Processes with Different $CO_2/(CO+CO_2)$ Ratios Hydrocarbons were produced by performing a Fischer-Tropsch synthesis process under the condition of a reaction temperature of 300° C. and a reaction pressure of 10 bar by loading 1 g of an iron-based catalyst with a composition of 100Fe-6Cu-16Al-4K in a ½-inch stainless steel fixed-bed reactor and supplying a synthesis gas at a flow rate of 1,800 mL/g cat·h. The hydrocarbon products were analyzed by on-line GC (TCD, FID).

The result of analyzing the selectivity of the hydrocarbon products depending on the composition of the synthesis gas used as a source material is shown in Table 1.

Example 2. Fischer-Tropsch Synthesis Processes with Different $H_2/(2CO+3CO_2)$ Values Fischer-Tropsch synthesis was conducted under the same condition as in Example 1 by fixing the $CO_2/(CO+CO_2)$ value to 0.5 and varying the $H_2/(2CO+3CO_2)$ value.

The result of analyzing the selectivity of the hydrocarbon products depending on the composition of the synthesis gas used as a source material is shown in Table 2.

TABLE 2

| | Molar ratio in synthesis gas | | CO → HC | Selectivity (%) | |
|---|---|---|---|---|---|
| | $CO_2/(CO+CO_2)$ | $H_2/(2CO+3CO_2)$ | conversion (%) | Hydrocarbon | $CO_2$ |
| Example 2-1 | 0.5 | 0.4 | 86.2 | 64.7 | 29.4 |
| Example 2-2 | 0.5 | 1 | 94.5 | 100.0 | −10.7 |

As seen from Table 2, when the $H_2/(2CO+3CO_2)$ molar ratio was 1, the hydrocarbon selectivity was 100%, the CO conversion was high and $CO_2$ was consumed. In contrast, when the $H_2/(2CO+3CO_2)$ molar ratio was low as 0.4, the CO conversion and the hydrocarbon selectivity were low and $CO_2$ was produced.

Example 3. Dehydrogenation Processes with Different Catalyst Conditions

Hydrocarbons produced by performing a Fischer-Tropsch synthesis process under the condition of a reaction temperature of 320° C. and a reaction pressure of 20 bar by loading 1 g of an iron-based catalyst with a composition of 100Fe-

TABLE 1

| | Molar ratio in synthesis gas | | Conversion (%) | | | Carbon deposition ratio (%) | $C_2$-$C_4$ hydrocarbon distribution (mol %) | |
|---|---|---|---|---|---|---|---|---|
| | $CO_2/(CO+CO_2)$ | $H_2/(2CO+3CO_2)$ | CO → HC | CO → $CO_2$ | $CO_2$ → HC | | $C_2$-$C_4$ | $C_2$-$C_4$ olefin |
| Example 1-1 | 0.25 | 1 | 96.8 | 19.7 | — | 5.9 | 32.3 | 72.7 |
| Example 1-2 | 0.4 | 1 | 95.5 | — | 8.7 | 5.4 | 31.2 | 73.1 |
| Example 1-3 | 0.5 | 1 | 95.0 | — | 12.6 | 4.7 | 30.1 | 73.7 |
| Example 1-4 | 0.6 | 1 | 94.1 | — | 17.6 | 4 | 29.4 | 74.2 |
| Example 1-5 | 0.75 | 1 | 88.4 | — | 29.7 | 3.1 | 28.0 | 75.1 |

According to the present invention, the Fischer-Tropsch (FT) process and the reverse water gas shift reaction proceeded well, the conversion of CO and $CO_2$ and the $C_2$-$C_4$ hydrocarbon selectivity were high and the carbon deposition ratio was low when the $CO_2/(CO+CO_2)$ molar ratio was 0.4-0.65 and the $H_2/(2CO+3CO_2)$ molar ratio was 1.

In contrast, when the $CO_2/(CO+CO_2)$ molar ratio was low as 0.25, the reverse water gas shift reaction did not occur although the carbon monoxide (CO) was converted to the $C_2$-$C_4$ hydrocarbon with a high conversion. And, when the $CO_2/(CO+CO_2)$ molar ratio was 0.75, the $C_2$-$C_4$ hydrocarbon selectivity was low because the CO conversion was decreased in the Fischer-Tropsch (FT) process.

6Cu-16Al-4K in a ½-inch stainless steel fixed-bed reactor and supplying a synthesis gas with $CO_2/(CO+CO_2)$=0.5 and $H_2/(2CO+3CO_2)$=1 at a flow rate of 1,800 mL/g cat·h were dehydrogenated. Before dehydrogenating the hydrocarbon products, $C_1$-$C_{15}$ short-chain hydrocarbons were separated through a separation process. The temperature and pressure inside the separator were maintained at 136° C. and 20 bar.

For the dehydrogenation, monocyclic aromatic compounds and long-chain olefin compounds were produced under the condition of a reaction temperature of 300° C. and a reaction pressure of 10 bar by loading 0.6 g of a crystalline aluminosilicate-based catalyst in a ½-inch stainless steel fixed-bed reactor. The composition of the products was analyzed by on-line GC (TCD, FID) and GC/MS.

The result of analyzing the composition of the hydrocarbon products depending on the composition of the catalyst used in the dehydrogenation process is shown in Table 3.

TABLE 3

|  | Main catalyst | Dehydrogenation condition | | | Product distribution (mol %) | | | |
|---|---|---|---|---|---|---|---|---|
|  |  | Promoter (A) | | | BTEX[1] | $C_6$-$C_{18}$ long-chain olefins | $C_6$-$C_{18}$ paraffin isomers | Other byproducts |
|  |  | Promoter | A/Al molar ratio |  |  |  |  |  |
| Example 3-1 | H-ZSM5[2] | — | — | 10.2 | 28.7 | 19.5 | 41.6 |
| Example 3-2 | H-ZSM5[3] | — | — | 19.9 | 22.3 | 13.1 | 44.7 |
| Example 3-3 | H-ZSM5[4] | — | — | 22.4 | 1.5 | 9.7 | 66.4 |
| Example 3-4 | H-ZSM5[4] | Zn | 0.3 | 14.8 | 4.2 | 19.2 | 61.8 |
| Example 3-5 | H-ZSM5[4] | Zn | 0.5 | 16.3 | 3.0 | 23.8 | 56.9 |

[1]BTEX: benzene, toluene, ethylbenzene and xylene
[2]H-ZSM5: Si/Al = 40, specific surface area = 454.6 m$^2$/g, Ratio of Brønsted to Lewis acid site = 1.21
[3]H-ZSM5: Si/Al = 25, specific surface area = 421.3 m$^2$/g, Ratio of Brønsted to Lewis acid site = 1.35
[4]H-ZSM5: Si/Al = 15, specific surface area = 402.1 m$^2$/g, Ratio of Brønsted to Lewis acid site = 0.81

As seen from Table 3, when only the crystalline aluminosilicate-based catalyst was used, the selectivity of monocyclic aromatic compounds was higher as the Si/Al ratio was smaller and the selectivity of long-chain olefin compounds was higher as the Si/Al ratio was larger.

And, when zinc (Zn) was included as a promoter while using the crystalline aluminosilicate-based catalyst as a main catalyst, the selectivity of paraffin isomers was increased in addition to those of the monocyclic aromatic compounds and the long-chain olefin compounds. This effect was enhanced as the Zn/Al ratio was increased.

Example 4. Dehydrogenation Processes with Different Temperature and Pressure Conditions Hydrocarbon produced by performing a Fischer-Tropsch synthesis process was dehydrogenated in the same manner as in Example 3. Before performing the dehydrogenation process, $C_1$-$C_{15}$ short-chain hydrocarbons were separated through a separation process.

For the dehydrogenation, monocyclic aromatic compounds and long-chain olefin compounds were produced by loading 0.6 g of a crystalline aluminosilicate-based catalyst in a fixed-bed reactor. The composition of the products was analyzed by on-line GC (TCD, FID) and GC/MS.

The result of analyzing the composition of the hydrocarbon products depending on the reaction temperature and reaction pressure conditions of the dehydrogenation process is shown in Table 4.

TABLE 4

|  | Dehydrogenation condition | | | Product distribution (mol %) | | |
|---|---|---|---|---|---|---|
|  | Reaction temperature (° C.) | Reaction pressure (bar) | Catalyst | BTEX[1] | $C_6$-$C_{18}$ long-chain olefins | Other byproducts |
| Example 4-1 | 300 | 1 | H-ZSM5[2] | 3 | 6.5 | 90.5 |
| Example 4-2 | 300 | 5 | H-ZSM5[2] | 22.0 | 1.9 | 76.1 |
| Example 4-3 | 300 | 10 | H-ZSM5[2] | 22.4 | 0.0 | 77.6 |
| Example 4-4 | 300 | 20 | H-ZSM5[2] | 18.4 | 0.6 | 81.0 |
| Example 4-5 | 250 | 20 | H-ZSM5[2] | 1.8 | 8.7 | 89.5 |
| Example 4-6 | 300 | 10 | Zn/H-ZSM5[3] | 16.3 | 1.5 | 82.2 |
| Example 4-7 | 350 | 10 | Zn/H-ZSM5[3] | 18.5 | 0.0 | 81.5 |
| Example 4-8 | 400 | 10 | Zn/H-ZSM5[3] | 13.9 | 1.6 | 84.5 |
| Example 4-9 | 450 | 10 | Zn/H-ZSM5[3] | 11.6 | 2.1 | 86.3 |

[1]BTEX: benzene, toluene, ethylbenzene and xylene
[2]H-ZSM5: Si/Al = 15, specific surface area = 402.1 m$^2$/g, Brønsted acid point = 0.81
[3]Zn/H-ZSM5: Si/Al = 15, Zn/Al = 0.5

As seen from Table 4, the selectivity of monocyclic aromatic compounds and long-chain olefin compounds in the products was changed by the reaction temperature and reaction pressure conditions of the dehydrogenation process. That is to say, when the reaction temperature was 300° C., the selectivity of monocyclic aromatic compounds was increased as the reaction pressure decreased below 10 bar. And, the selectivity of long-chain olefin compounds was the highest when the reaction condition was 250° C. and 20 bar.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for synthesizing monocyclic aromatic compounds and long-chain olefin compounds from a carbon dioxide-rich synthesis gas, the method comprises:
   i) preparing a hydrocarbon by conducting a Fischer-Tropsch (FT) synthesis process in the presence of an iron-based catalyst using a carbon dioxide-rich synthesis gas with a $CO_2/(CO+CO_2)$ molar ratio controlled within a range from 0.4 to 0.65 as a source material;
   ii) separating a $C_1$-$C_{15}$ short-chain hydrocarbon from the hydrocarbon products; and
   iii) preparing $C_6$-$C_{12}$ monocyclic aromatic compounds and $C_6$-$C_{18}$ long-chain olefin compounds by dehydrogenating the $C_1$-$C_{15}$ short-chain hydrocarbon in the presence of a crystalline aluminosilicate-based catalyst, hydrogen and water,
   wherein the crystalline aluminosilicate-based catalyst in the step iii) has a Si/Al molar ratio of 10-50 and comprises mesopores with a size of 10 nm or smaller and micropores with a size of 1-8 Å, and
   wherein the crystalline aluminosilicate-based catalyst in the step iii) has a Brønsted acid site/Lewis acid site ratio of 0.1-3.2.

2. The method for synthesizing monocyclic aromatic compounds and long-chain olefin compounds according to claim 1, wherein the carbon dioxide-rich synthesis gas in the step i) has a $H_2/(2CO+3CO_2)$ molar ratio of 0.85-1.1.

3. The method for synthesizing monocyclic aromatic compounds and long-chain olefin compounds according to claim 1, wherein the iron-based catalyst in the step i) further comprises one or more promoter selected from a group consisting of copper (Cu), manganese (Mn), cobalt (Co), nickel (Ni), zinc (Zn), aluminum (Al) and potassium (K).

4. The method for synthesizing monocyclic aromatic compounds and a long-chain olefin compounds according to claim 1, wherein the step i) is performed under the condition of a reaction temperature of 250-350° C. and a reaction pressure of 10-30 bar.

5. The method for synthesizing monocyclic aromatic compounds and long-chain olefin compounds according to claim 1, wherein, in the step ii), a $C_4$-$C_{15}$ short-chain hydrocarbon is separated at a temperature of 0-200° C. based on a pressure of 20 bar.

6. The method for synthesizing monocyclic aromatic compounds and long-chain olefin compounds according to claim 1, wherein the step iii) is performed under the condition of a reaction temperature of 100-450° C. and a reaction pressure of 1-30 bar.

7. The method for synthesizing monocyclic aromatic compounds and long-chain olefin compounds according to claim 6, wherein the step iii) is performed under the condition of a reaction temperature of 300-350° C. and a reaction pressure of 5-20 bar to maximize the selectivity of the monocyclic aromatic compounds.

8. The method for synthesizing monocyclic aromatic compounds and long-chain olefin compounds according to claim 6, wherein the step iii) is performed under the condition of a reaction temperature of 200-270° C. and a reaction pressure of 10-20 bar or a reaction temperature of 300-350° C. and a reaction pressure of 1-2 bar to maximize the selectivity of the long-chain olefin compounds.

9. The method for synthesizing monocyclic aromatic compounds and long-chain olefin compounds according to claim 1, wherein the crystalline aluminosilicate-based catalyst in the step iii) further comprises one or more promoter metal element (A) selected from a group consisting of iron (Fe), copper (Cu), zinc (Zn), tin (Sn), nickel (Ni), molybdenum (Mo), potassium (K), lanthanum (La), platinum (Pt), gold (Au), palladium (Pd), rhodium (Rd), ruthenium (Ru) and silver (Ag).

10. The method for synthesizing a monocyclic aromatic compound and a long-chain olefin compound according to claim 9, wherein the A/Al molar ratio of the promoter metal element (A) based on the aluminum (Al) atom of the crystalline aluminosilicate-based catalyst is 0.01-2.5.

11. The method for synthesizing monocyclic aromatic compounds and long-chain olefin compounds according to claim 1, wherein, in the step iii), the molar ratio of hydrogen is 0.1-10 and the molar ratio of water is 0.1-1.3 based on the short-chain hydrocarbon.

12. The method for synthesizing monocyclic aromatic compounds and long-chain olefin compounds according to claim 1, wherein, in the step iii), a $C_1$-$C_4$ light hydrocarbon produced as a byproduct is recycled to a reforming process for preparing the synthesis gas.

* * * * *